United States Patent

Cheburkov et al.

Patent Number: 5,723,630
Date of Patent: Mar. 3, 1998

[54] PROCESS FOR PREPARING FLUORINATED BETA-SULTONES

[75] Inventors: Yuri Cheburkov, Woodbury; William M. Lamanna, Stillwater, both of Minn.

[73] Assignee: Minnesota Mining and Manufacturing Company, St. Paul, Minn.

[21] Appl. No.: 802,193

[22] Filed: Feb. 18, 1997

[51] Int. Cl.$^6$ .................................................. C07D 331/04
[52] U.S. Cl. ................................................................ 549/89
[58] Field of Search ................................................. 549/89

[56] References Cited

U.S. PATENT DOCUMENTS

| | | | |
|---|---|---|---|
| 3,041,317 | 6/1962 | Gibbs et al. | 260/79.3 |
| 3,862,971 | 1/1975 | Rudolph et al. | 260/408 |
| 4,206,138 | 6/1980 | England | 260/458 F |
| 4,505,997 | 3/1985 | Armand et al. | 429/192 |
| 4,959,490 | 9/1990 | Parnell et al. | 562/74 |
| 5,072,040 | 12/1991 | Armand | 564/82 |
| 5,300,714 | 4/1994 | Pothapragada et al. | 570/179 |
| 5,318,674 | 6/1994 | Behr et al. | 204/59 |
| 5,486,271 | 1/1996 | Hansen et al. | 204/59 F |

FOREIGN PATENT DOCUMENTS 0 670 294    9/1995    European Pat. Off. .

OTHER PUBLICATIONS

Childs et al., "Anodic Fluorination," Organic Electrochemistry, Marcel Dekker, Inc., pp. 1103–1127, 1991.

Brochure entitled "Sulfur Trioxide and Oleum," (26 pages), 1987.

Gibbs et al., "Preparation and Properties of 2-Hydroperfluoroalkyl Fluosulfonates," J. Am. Chem. Soc., vol. 26, pp. 4140–4141, 1961.

Krespan et al., "Fluorosulfonation. Insertion of Sulfur Trioxide into Allylic C–F Bonds," J. Org. Chem., vol. 51, pp. 4460–4466, 1986.

Sokol'skii et al., "Fluorine–Containing β–Sultones, Communication 25. Stabilization of Liquid Sulfur Trioxide," pp. 807–809, Izvest. Akad.SSSR, 1968.

Sidgwick, "The Chemical Elements and Their Compounds," vol. 2, 898–903, 1950, Clarendon Press.

Adcock, "Replacement of Hydrogen by Fluorine," Chemistry of Organic Fluorine Compounds II, pp. 97–119, 1995.

Mohtasham et al., "β–Fluorosultones: synthesis, reactivity, structure and uses," Coordination Chemistry Reviews, 112, pp. 47–79, 1992.

Yamabe et al., "Fluorinated Membranes," Organofluorine Chemistry, pp. 403–411, 1994.

Knunyants et al., "Fluorinated β–Sultones," Ang. Chem. Int. Ed., vol. 11, No. 7, pp. 583–595, 1972.

Alsmeyer, et al., "Electrochemical Fluorination and Its Applications," Organofluorine Chemistry, pp. 121–133, 1994.

England et al., "Reactions of Fluoroolefins with Sulfur Trioxide," vol. 82, pp. 6181–6188, 1960.

Hsi–Kwei Jiang, "Addition reactions of Sulfur Trioxide to Carbon–Carbon Double Bonds," 10 Organic Chemistry, 15493, 1958.

Storzer et al., Inorganic Chemistry, vol. 30, pp. 4821–4826, 1991.

Primary Examiner—José G. Dees
Assistant Examiner—Mary C. Cebulak
Attorney, Agent, or Firm—Daniel C. Schulte

[57] ABSTRACT

A process allows the preparation of a fluorinated beta-sultone by reacting a fluorinated olefin with oleum.

19 Claims, No Drawings

PROCESS FOR PREPARING FLUORINATED BETA-SULTONES

FIELD OF THE INVENTION

This invention relates to a process for preparing fluorinated beta-sultones, and further to processes for preparing other compounds by converting the fluorinated beta-sultones to compounds such as fluoroalkylsulfonyl fluorides and fluoroalkyl sulfonic acids.

BACKGROUND

Fluorinated beta-sultones are commercially valuable chemical compounds. Fluorinated beta-sultones exhibit utility as chemical intermediates, and therefore can be processed (e.g., hydrolyzed and/or fluorinated) to produce other valuable chemical compounds such as fluoroalkylsulfonyl fluorides, fluoroalkyl sulfonic acids, and perfluorinated analogs of each of these. See for example I. L. Knunyants and G. A. Sokolski, Fluorinated β-Sultones, Ang. Chemie, Intnl. Ed., vol 11 p. 583 (1972); and Y. Mohtasham et al. in β-Fluorosultones: synthesis, reactivity, structure and uses, Coordination Chemistry Reviews, 112 p. 47–79 (1992).

The usefulness offluoroalkylsulfonyl fluorides is well documented, and includes their application in the production of perfluoroalkanesulfonamides (which are useful as herbicides, antimicrobials, and antiobesity drugs), as well as salts such as lithium perfluoroalkanesulfonates and lithium bis(perfluoroalkanesulfonyl)imides (which are useful as electrolyte salts for battery applications). See e.g., U.S. Pat. Nos. 5,318,674 (Armand et al.), 4,505,997 (Armand et al.), and 5,072,040 (Armand et al.).

Fluoroalkylsulfonyl fluorides can also be further hydrolyzed and/or fluorinated to produce monomeric and polymeric fluoroalkylsulfonic acids, and their perfluorinated analogs. Fluoroalkylsulfonic acids are known to have many useful applications, including as catalysts, when polymerized as ion exchange resins and perfluorinated membranes (e.g., as Nafion ™ ion exchange membranes), and as separators for electrochemical processing (see M. Yamabe and H. Miyake, Fluorinated Membranes, *Organofluorine Chemistry: Principles and Commercial Applications*, pp 403–411 (1994).

Fluorinated beta-sultones are conventionally prepared by reacting a fluorinated olefin with a very pure form ofmonomeric sulfur trioxide ($SO_3$). See, e.g., U.S. Pat. No. 3,041,317 (Gibbs et al.). This reaction suffers serious practical drawbacks. For instance, the reaction of pure, monomeric sulfur trioxide with a number offluoroolefins (e.g., hexafluoropropene and chlorotrifluoroethylene) to produce a fluorinated beta-sultone is often performed at relatively high reaction temperatures, e.g., up to about 100° or 150° C.

Another drawback relating to the production offluorinated beta-sultones from pure sulfur trioxide stems from the understanding that in order to effectively produce a fluorinated beta-sultone, one must use only very pure, freshly-distilled, sulfur trioxide as a reactant. Investigators have been discouraged when reacting a fluorinated olefin with sulfur trioxide that contains even a minor amount of water. These investigators strongly emphasize the need for "freshly distilled sulfur trioxide." For instance, a small amount of water present in sulfur trioxide, when reacted with a fluorinated olefin, has been observed to produce undesired reaction products, and to reduce the amount of the desired fluorinated beta-sultone produced. See Mohtasham and Gard, Coordination Chemistry Reviews, 112 pp. 47–79 (1992) at p. 49 (stating that "[i]mpurities such as water [present in monomeric $SO_3$] can lower the overall yield of the sultone or produce side products "); England, Dietrich and Lindsey, Reactions of Fluoroolefins with Sulfur Trioxide, J. Am. Chem. Soc., 82, pp. 6181–88, (1960) at p. 6183 (indicating that water in "stabilized sulfur trioxide" produces polymerized $SO_3$, which inhibits the production of beta-sultone when reacted with tetrafluoroethylene). Accordingly, conventional wisdom holds that in the production offluorinated beta-sultones from a fluoroolefin and sulfur trioxide, "it is important always to start with freshly distilled and pure $SO_3$." Mohtasham at p. 49.

The need for very pure, monomeric $SO_3$ creates great practical inconvenience in the production offluorinated beta-sultones, and poses serious safety concerns. Sulfur trioxide has a relatively high vapor pressure, and therefore must be transferred and stored in specially designed containers capable of withstanding such pressure. Additionally, sulfur trioxide is relatively unstable towards polymerization, and is difficult to de-polymerize. In industry, costly and inconvenient precautions are taken to prevent such uncontrolled polymerization. Containers used to store and transport pure or relatively pure $SO_3$ must be unfailingly maintained at elevated temperatures in the range from about 35° to 41° C. As a further precaution against polymerization, commercially available $SO_3$ often contains polymerization reaction inhibitors. Such inhibitors can work well in preventing polymerization, but unfortunately can also inhibit the ability of the $SO_3$ to react with other chemical compounds to produce useful reaction products such as sultones. Therefore in practice, pure, monomeric sulfur trioxide that contains a polymerization inhibitor is generally distilled to remove that inhibitor before the sulfur trioxide can be reacted with an olefin to produce a fluorinated beta-sultone.

Of course all of the above-described safety precautions and purification steps increase the cost and inconvenience and reduce the efficiency of processes that use pure, monomeric $SO_3$ as a reactant for producing a fluorinated beta-sultone. Because of the known disadvantages relating to the use of pure $SO_3$, including the expense and inconvenience, it would be desirable to find a process of preparing fluorinated beta-sultones, fluorinated sulfonyl fluorides, fluorinated sulfonic acids, and each of their respective perfluorinated analogs, etc., without the requirement of using purified, monomeric, sulfur trioxide.

SUMMARY OF THE INVENTION

The process of the present invention provides a method of preparing fluorinated beta-sultones by reacting a fluorinated olefin with oleum. Unlike pure, monomeric, sulfur trioxide, oleum does not generally polymerize upon standing, or upon exposure to moisture. Also in contrast to pure, monomeric sulfur trioxide, there is no need to precisely control the temperature of oleum during transport and storage, or to add reaction inhibitors which must be removed prior to reacting the oleum to produce a fluorinated beta-sultone. Thus, the use of oleum can reduce the overall cost of producing fluorinated beta-sultones by eliminating costly safety precautions and burdensome processing steps.

An aspect of the present invention relates to a process for preparing a fluorinated beta-sultone by reacting a fluorinated olefin with oleum. Preferably, the fluorinated olefin is a 1,1-difluoro terminal olefin. The produced fluorinated beta-sultone can be isolated and used as in any application known for fluorinated beta-sultones. Alternatively, the fluorinated beta-sultone can be further processed to produce a number of different and useful chemical compounds. As an example, the fluorinated beta-sultone can be hydrolyzed to form a fluoroalkylsulfonyl fluoride. This fluoroalkylsulfonyl fluoride can be further hydrolyzed (generally under basic conditions) to produce a salt of a fluoroalkyl sulfonic acid, which can be re-acidified to produce a fluoroalkyl sulfonic acid. Any of these reaction products, if not fully fluorinated, can optionally be fluorinated to produce a more highly fluorinated, or a perfluorinated chemical analog.

A further aspect of the present invention is a method for producing a fluoroalkylsulfonyl fluoride. A fluorinated olefin is reacted with oleum to produce a fluorinated beta-sultone. The fluorinated beta-sultone is hydrolyzed under conditions sufficient to produce a fluoroalkylsulfonyl fluoride.

Yet a further aspect of the present invention is a method for producing a fluoroalkyl sulfonic acid. A fluorinated olefin is reacted with oleum to produce a fluorinated beta-sultone. The fluorinated beta-sultone is hydrolyzed to produce a fluoroalkyl sulfonyl fluoride, which is further hydrolyzed to a fluoroalkyl sulfonic acid salt or a fluoroalkyl sulfonic acid.

As used in the present description, the term "pure sulfur trioxide" or "pure $SO_3$" refers to monomeric sulfur trioxide that is at least about 95% by weight pure, for example 99 wt % pure, without respect to the presence of any polymerization inhibitors;

DETAILED DESCRIPTION

According to the present invention a fluorinated olefin can be reacted with oleum to produce a fluorinated beta-sultone. The oleum and fluorinated olefin (the "reactants") can be combined, optionally in the presence of a solvent, to form a reaction solution that can be exposed to conditions sufficient to cause the two reactants to react to form a fluorinated beta-sultone. As used within the present description, the term "reaction solution" refers to a chemical composition (e.g., mixture, solution, or dispersion, etc.) generally containing one or more of a fluorinated olefin and oleum, optionally a solvent, and possibly one or more reaction products of the reactants.

In general, the fluorinated olefin can be any fluorinated olefin that, according to the present invention, can be reacted with oleum to yield a fluorinated beta-sultone. Fluorinated olefins that have been found to be useful include 1,1,-difluoro terminal olefins such as those generally described by formula (1):

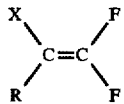

(1)

In Formula 1, X is F or H, and K can be any of a straight of branched alkyl group; a straight or branched haloalkyl group (a group containing one or more carbon-bonded halogens such as fluorine or chlorine); or a straight or branched perhaloalkyl group (a group containing carbon-bonded halogens such as fluorine or chlorine, and no carbon-bonded hydrogens). The carbon chain backbone of the R group can optionally be interrupted by one or more non-vinylic heteroatoms such as sulfur, oxygen, or nitrogen. Such interrupted R groups can generally be useful if the K group is substantially non-reactive toward oleum; i.e., R is sufficiently stable in oleum that when the olefin is reacted with oleum, an amount of the vinylic portion of the olefin will react with the sulfur trioxide to form a useful amount of sultone. Specifically, in R groups that contain one or more of a non-vinylic sulfur or nitrogen atom, the additional valences of the sulfur or nitrogen atom(s) can be substituted to render the R group unreactive toward oleum. This can be accomplished, for instance, by ensuring that the heteroatom is not bonded to any hydrogen atoms. The heteroatom might be bonded to only halogens such as with —$SF_5$ or —$SF_4Cl$. Alternatively, the heteroatom might be bonded to a nonhalogen R' group that will render R the stable in oleum. Such R' groups generally include perhaloalkyl groups, as well as haloalkyl group wherein no hydrogen atoms are located alpha to the heteroatom. As a specific example, R" can be —$CXXR'$ wherein each X is independently a halogen, and wherein R" can independently be a halogen, a haloalkyl, or a perhaloalkyl.

Preferably, in the 1,1-difluoro terminal olefin of Formula 1, X is F and R is haloalkyl, or perhaloalkyl group having from about 1 to 10 carbon atoms, more preferably from about 1 to 6 carbon atoms, and optionally interrupted by one or more non-vinylic sulfur or oxygen atoms. Examples of such 1,1-difluoro terminal olefins include:

| | |
|---|---|
| $CF_3CF=CF_2$ | $CF_2ClCFClCF_2CF=CF_2$ |
| $C_4F_9CF=CF_2$ | $CF_3OCF_2CF=CF_2$ |
| $C_5F_{11}CF=CF_2$ | $CF_3OCF_2CF_2OCF_2CF=CF_2$ |
| $CHF_2CF=CF_2$ | $(CF_3)_2CFOCF_2CF=CF_2$ |
| $H(CF_2)_4CF=CF_2$ | $SF_5CF=CF_2$ |
| $C_4H_9CF=CF_2$ | $SF_4ClCF=CF_2$ |
| $CH_2ClCHClCH_2CF=CF_2$ | $CF_3CH=CF_2$ |
| | $SF_5CH=CF_2$ | with hexafluoropropene (HFP), 6H-perfluoro-1-hexene, and 2H-pentafluoropropene (PFP) being preferred. These and other fluorinated olefins can be synthesized by methods known in the fluorochemical art, and many are commercially available from sources including PCR Inc. of Gainesville Fla.; Halocarbon Products Corp. of River Edge, N.J.; DuPont Chemicals of Wilmington, Del.; Daikin, of Japan; and ICI Chemicals and Polymers Ltd. Of Great Britain, among others.

Throughout the present description the term "oleum" refers to what is commonly described in the chemical art as "fuming sulfuric acid," which contains sulfur trioxide ($SO_3$) dissolved in sulfuric acid ($H_2SO_4$), and which generally consists essentially of sulfur trioxide dissolved in sulfuric acid. The oleum can contain any amount of $SO_3$ and $H_2SO_4$ that will be effective to react with a fluorinated olefin to produce a fluorinated beta-sultone, and that is preferably stable at room temperature (e.g., not susceptible to polymerization). For example the oleum can contain less than about 75 parts by weight $SO_3$ per 25 parts by weight $H_2SO_4$, more preferably from about 50 to 70 parts by weight $SO_3$ per 50 to 30 parts by weight $H_2SO_4$, respectively, and even more preferably from about 60 to 70 parts by weight $SO_3$ per 40 to 30 parts by weight $H_2SO_4$, respectively. Oleum is often commercially available in concentrations of about e.g., 20, 25, 30, and up to 65 or 67 wt % $SO_3$ in $H_2SO_4$, for example from DuPont Chemicals of Wilmington, Del.

In the practice of the present invention the fluorinated olefin and the oleum (especially with respect to its sulfur trioxide component) can be combined in any relative amounts that will result in a reaction between the sulfur trioxide and the fluorinated olefin to produce a fluorinated beta-sultone. The chosen amounts of oleum/sulfur trioxide and fluorinated olefin can be selected based on a number of factors, including the specific fluorinated olefin used, the presence and identity of any solvent, the desired fluorinated beta-sultone reaction product, etc. Without wishing to be bound by theory, it is believed that the sulfur trioxide portion of the oleum is responsible for reacting with the fluorinated olefin to produce the fluorinated beta-sultone. Thus, the amount of oleum that can be added to the reaction solution depends in great part upon the concentration of sulfur trioxide contained in the oleum. In very general terms, preferred molar ratios of sulfur trioxide (as calculated to be in the oleum) versus fluorinated olefin within the reaction solution can be in the range from about 1:2 to 2:1, with a particularly preferred range being from about 9:10 to 10:9.

Additionally, the relative amounts of the fluorinated olefin and the oleum can be selected based on the expected post-reaction processing to be performed on the reaction solution, for instance, depending upon which reactant is most desirably in excess in the reaction solution during such post-reaction processing (e.g., separation, distillation steps, etc.). The desired post-reaction processing can in turn depend upon whether the produced fluorinated beta-sultone is the desired reaction product, or whether the fluorinated beta-sultone will be further reacted (e.g., hydrolyzed and/or fluorinated) to produce another chemical compound such as a fluoroalkyl sulfonyl fluoride or a fluoroalkyl sulfonic acid.

In some instances the fluorinated olefin is preferably reacted with oleum wherein the sulfur trioxide is present in molar excess with respect to the olefin. This is because oleum is relatively inexpensive, and because reaction of the fluorinated olefin in excess sulfur trioxide tends to produce higher yields of fluorinated beta-sultone. Excess sulfur trioxide is often desirable if the fluorinated beta-sultone is not the desired final reaction product, but will be further processed to form a fluoroalkyl sulfonyl fluoride or a fluoroalkyl sulfonic acid. In these cases oleum (e.g., 65 wt % $SO_3$ in $H_2SO_4$) can be used in an amount sufficient to provide a molar excess of sulfur trioxide, and is preferably combined with the fluorinated olefin to produce a reaction solution having from about 5 to 10% molar excess of sulfur trioxide with respect to the fluorinated olefin.

In other situations oleum (i.e., the sulfur trioxide component) is preferably reacted with a molar excess offluorinated olefin. Excess fluorinated olefin may be desirable in situations where, for example, the desired fluorinated beta-sultone reaction product has a boiling point similar to the boiling point of sulfur trioxide. This specific situation exists when hexafluoropropene and oleum are reacted to produce hexafluoropropene beta-sultone. During or following the reaction, the desired hexafluoropropene beta-sultone may desirably be separated from the reaction solution. Unfortunately, hexafluoropropene beta-sultone has a boiling point that is similar to the boiling point of sulfur trioxide. Thus, it can be difficult to separate the hexafluoropropene beta-sultone from an excess amount of sulfur trioxide. The use of excess fluorinated olefin results in relatively complete reaction of the sulfur trioxide, thus reducing the amount of sulfur trioxide that will be present in the reaction solution upon completion of the reaction, and reducing or eliminating the need to separate the desired hexafluoropropene beta-sultone from sulfur trioxide. When used in excess, the fluorinated olefin can be present in any excess amount, but is preferably present in an amount in the range from about 5 to 10 percent molar excess compared to the sulfur trioxide in the oleum.

In the practice of the present invention, the reaction solution can also contain an optional solvent which, if chosen to be present, can be inert to the reactants, can dissolve or disperse the reactants, and can preferably moderate the heat of the reaction. Also preferably the solvent can be one that facilitates (or at least does not hinder) separation of the fluorinated beta-sultone reaction product from the reaction solution. Although it will be apparent to those skilled in the fluorochemical art that a wide variety of solvents will exhibit such properties, examples of useful solvents include perfluoroalkanes such as perfluorohexane or perfluorooctane; perfluoroethers and perfluoro cyclic ethers, including as perfluoro-2-butyltetrahydrofuran; perfluoroamines such as perfluoro tripropyl amine or perfluoromorpholine; and mixtures of the above-identified solvents. Particularly preferred solvents can comprise a mixture of perfluoro cyclic ethers. Such solvent mixtures are commercially available, for example from the 3M Company of St. Paul Minn., under the trade name Fluorinert FC-77™.

The reactants and optional solvent can be combined to form a reaction solution in any reaction vessel that will allow the production of a fluorinated beta-sultone. Examples of useful reaction vessels include reaction vessels that can be operated at atmospheric pressure such as glass round-bottom flasks, as well as pressurized reaction vessels including sealed glass tubes and pressure vessels constructed of metal. The reaction can preferably be performed in a reaction vessel that includes some type of means for agitating the reaction solution, such as a mechanical stirrer or agitator.

The fluorinated olefin, the oleum, and any optional solvent can be charged to the reaction vessel in any order of addition, and under any conditions that are effective to result in the production of a fluorinated beta-sultone. As an advantage of the use of oleum over purified sulfur trioxide, the oleum can be cooled and/or exposed to ambient moisture without the risk of polymerization associated with pure, monomeric sulfur trioxide. Because of this ability to charge oleum at reduced temperature, it also becomes possible to charge the olefin at reduced temperature, e.g., to charge the olefin as a liquid if desired or convenient.

Once charged, the reaction solution can be reacted under any effective reaction conditions (reaction temperature, pressure, timing, etc.). Reaction conditions can vary, and can be chosen according to a variety of factors including the particular reactants chosen (the fluorinated olefin and the chosen concentration of sulfur trioxide in the oleum); whether or not a solvent is present in the reaction solution, and if so the identity of the solvent; the desired reaction product or products; the desired yield offluofinated beta-sultone; properties and limitations of the reaction equipment; etc. In general, it has been found that the oleum can be reacted with a fluorinated olefin under relatively mild reaction conditions to produce a fluorinated beta-sultone.

According to one embodiment of the present invention, a fluorinated beta-sultone has been prepared by bubbling a fluorinated olefin through oleum at room temperature and at atmospheric pressure. This method has been found to be especially useful in the preparation of 2H-pentafluororopane beta-sultone, by reacting 2H-pentafluoropropene with oleum. Although such mild conditions can be useful, somewhat higher temperatures and pressures can also be useful. For example in another embodiment a fluofinated beta-sultone has been prepared by reacting oleum with a fluorinated olefin at a reaction temperature of about 35° C., a reaction pressure of about 100 psi (690 kPa) and for reaction times in the range from about 2 to 3 hours. In still another embodiment, a fluorinated beta-sultone has been prepared in a pressurized reactor, at autogenous pressure and temperature; i.e., the vessel was charged with reactants at ambient pressure, sealed, and the pressure and temperature inside the sealed vessel were allowed to increase in response to the progress of the reaction.

With specific regard to useful reaction temperatures, the reaction temperature can be, for example, ambient temperature (about 25° C.), or any elevated temperature such as 50°, 100°, or 150° C. The reaction temperature can be maintained at its initial reaction temperature, or its charge temperature, throughout the course of the reaction. Or, the reaction temperature can vary throughout the course of the reaction. The reaction of the present invention is moderately exothermic and therefore, unless some or all of the evolved heat energy is removed from the reaction solution, the temperature of the reaction solution will increase as the reaction proceeds. It has been found to be useful to begin with a reaction solution at ambient temperature and thereafter allow the reaction solution temperature to increase with the exothermic release of energy. In general there is no need to supply additional heat energy to the reaction solution. However, upon reaching a peak reaction temperature, heat energy can optionally be added to the reaction solution to maintain that peak temperature, if desired, through a portion or through completion of the remaining reaction.

With specific regard to useful reaction pressures, the reaction can be performed at any effective reaction pressure, e.g., ambient pressure (760 mmHg) or any elevated pressure. The reaction pressure can remain constant over the course of the reaction, or can vary throughout the course of the reaction (e.g., autogenously or otherwise).

The time allowed for the reaction can be any effective reaction time and can vary with the factors generally affecting reaction conditions described above. In general the reaction time can be any time needed to produce a useful amount of a fluorinated beta-sultone. The actual reaction time can range from a very short, nearly instantaneous time period, to a period of several hours, depending on the exact reaction being performed, the chosen reaction conditions, the reaction vessel, etc.

In one particularly preferred embodiment of the present invention, reactants and any optional solvent can be added to a pressure vessel at ambient pressure, and the reaction vessel can be sealed. As the reaction proceeds, pressure and temperature within the sealed reaction vessel increase. The ultimate autogenous pressure and the ultimate temperature of the reaction solution will depend on factors such as the relative amounts of each reactant used, the presence of a solvent, the identities of reactants and solvent, the size and heat flow characteristics of the reaction vessel, etc. As a single example, when 62 grams hexafluoropropene are reacted with 64 grams oleum (65 wt % $SO_3$ in $H_2SO_4$) inside of a 100 mL pressure vessel starting at low temperature (−30 C.) and ambient pressure, a temperature of about 50° C. and a pressure of about 130 psi (900 kPa) can be reached during the reaction. This reaction can be effectively complete in a time period in the range from about 2 to 3 hours.

The particular fluorinated beta-sultone produced by the reaction of the present invention will depend in large part on the identity of the fluorinated olefin chosen as the reactant. In general, the fluorinated beta-sultone will be of the formula:

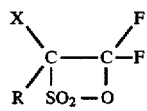  (2)

wherein X and R are as defined above with respect to the fluorinated olefin of formula 1. As specific examples of fluorinated beta-sultones that can be produced according to the present invention, the following fluorinated beta-sultones can be produced by reacting oleum with hexafluoropropene, 2H-pentafluoropropene, and 6H-perfluoro-1-hexene,respectively: 2-hydroxy-1-trifluoromethyl-1,2,2-trifluoroethanesulfonic acid suitone ($R=CF_3$ and $X=F$; also referred to herein as hexafluoropropene beta-sultone or HFP sultone)

  (2.1)

2-hydroxy-1-trifluoromethyl-2,2-difluoroethanesulfonic acid suitone ($R=CF_3$ and $X=H$; also referred to herein as 2H-pentafluoropropene beta-sultone or PFP sultone)

  (2.2)

and 2-hydroxy-1-(4H-perfluorobutyl)-1,2,2-trifluoroethanesulfonic acid suitone ($R=H(CF_2)_4$ and $X=F$; also referred to herein as 6H-perfluoro-1-hexene beta-sultone)

  (2.3)

The yield of fluorinated beta-sultone produced can be expressed and is defined herein as the amount (moles) offluorinated beta-sultone produced per the amount (moles) offluorinated olefin consumed ("consumed fluorinated olefin"). The consumed fluorinated olefin is the amount (moles) offluorinated olefin added to the reaction solution as a reactant, less the amount (moles) offluorinated olefin remaining upon completion of the reaction. The actual yield of fluorinated beta-sultone achieved by any particular reaction will depend on a number of factors including the reactants chosen; the amount and identity of any solvent used; the reaction apparatus, e.g., the use of a pressurized vessel, or an open vessel; and reaction conditions including temperature, pressure, and timing. By way of example, the yield offluorinated beta-sultone based on the amount of consumed fluorinated olefin can be at least 50%, and is preferably 60%, more preferably 70% or more.

It is important to note that fluorinated beta-sultones are not the only reaction products of the reaction between a fluorinated olefin and oleum. A number of side-reactions can also produce useful reaction products. As an example, the reaction ofhexafluoropropene with oleum can produce tetrafluoropropionic acid fluorosulfate:

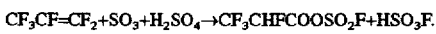

Another example is the reaction between pentafluoropropene and fluorosulfonic acid, leading to the formation of a fluorosulfonic acid ester.

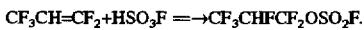

As will be appreciated by those skilled in the fluorochemical art, other analogous reaction products and derivatives can be produced from the reaction of the components of oleum ($H_2SO_4$ and $SO_3$) with other fluorinated olefins.

Generally, upon completion of the reaction, the reaction solution will have separated into two distinct layers within the reaction vessel: an upper layer (described herein as the "sultone" layer) containing primarily the fluorinated beta-suitone product, possibly a small amount of unreacted sulfur trioxide (depending on the amount added to the reaction solution), and small amounts of other organic by-products such as fluoroalkyl fluorosulfates; and a "lower" layer containing a variety of reaction products such as fluorosulfonic acid, sulfuric acid, and fluorosulfates.

The method of the present invention can include a step of separating the sultone layer from the lower layer, and also a step of isolating the desired beta-suitone reaction product from the sultone layer. Methods to accomplish these steps are very well known in the chemical art. Examples include mechanical techniques (e.g., decantation), and chemical techniques such as distillation. In the case of hexafluoropropene beta-sultone, it has been found that this compound can be distilled directly from the reaction solution without first separating the sultone layer from the lower layer. In some other situation, however, it may be desirable to first perform a separation step wherein the sultone layer is separated from the lower layer.

As another (optional) processing step, the sultone layer can be washed with sulfuric acid to remove undesired chemical compounds such as sulfur trioxide and/or fluorosulfonic acid. The washing step can preferably be performed after the separation step, prior to a distillation step. If the fluorinated beta-sultone will later be distilled from the sultone layer, it can be preferable to wash the sultone layer with sulfuric acid prior to distillation in order to remove sulfur trioxide. This is especially true if the fluorinated beta-sultone has a boiling point that is near the boiling point of sulfur trioxide; the removal of the sulfur trioxide prior to distillation facilitates purification of the fluorinated beta-sultone by eliminating or reducing the potential for co-distillation of sulfur trioxide with the fluorinated beta-sultone.

In the practice of the present invention, the fluorinated beta-sultone, either prior to or following its isolation from the reaction solution, can be further reacted to produce other useful chemical compounds. For example, the fluorinated beta-sultone can be hydrolyzed with water to produce a fluoroalkylsulfonyl fluoride or a fluoroalkyl sulfonic acid. Hydrolysis with neutral or acidic water can produce fluoroalkylsulfonyl fluorides, while hydrolysis with aqueous base can produce fluoroalkylsulfonic acid salts. Such methods are well known in the fluorochemical art (see Knunyants and Sokolski, supra). Although hydrolysis can be accomplished without a separation step, separation of the suitone layer from the lower layer prior to adding the suitone layer to water can be preferred. Specific fluoroalkylsulfonyl fluorides (or their corresponding fluoroalkyl sulfonic acids) that can be produced by the method of the present invention include 1H-tetrafluoroethanesulfonyl fluoride, 2,2,2-trifluoroethanesulfonyl fluoride, 1,5-dihydrononafluoropentanesulfonyl fluoride. Especially preferred is 1H-tetrafluoroethanesulfonyl fluoride.

As yet a further (optional) processing step, any of the described reaction products, e.g., the fluorinated suitone, fluoroalkylsulfonyl fluoride, or fluoroalkyl sulfonic acid, can be fluorinated to produce a corresponding more highly fluorinated compound, or a corresponding perfluorinated compound. Fluorination can be accomplished by any of a number of useful fluorination methods that are known in the fluorochemical art, including direct fluorination and electrochemical fluorination. Examples of useful fluorination methods are described, for example, in U.S. Pat. Nos. 5,486,271 (Hansen et al.); and R. E. Banks, et al., *Organofluorine Chemistry, Principles and Commercial Applications*, pp. 121–133 (1994) each of which is incorporated herein by reference. Also, fluorination of a fluorinated beta-sultones prepared by the method of the present invention according to U.S. Pat. No. 5,318,674 (Behr et at., also incorporated herein by reference), can produce perfluoroalkanesulfonyl fluorides, including specifically, perfluoroethanesulfonyl fluoride.

The present invention will now be described in terms of the following non-limiting examples.

EXAMPLE 1

Preparation of HFP suitone from the reaction of hexafluoropropene with oleum having excess $SO_3$, at elevated pressure A 100 mL Parr™ reactor was charged with 63.8 g of 65% oleum (0.52 mole $SO_3$), cooled to $-45°$ C., evacuated, and then charged with 62 grams (0.44 mole) liquid hexafluoropropene from a cold trap ($-78°$ C.). The reaction mixture was allowed to warm to room temperature. At 20° C. a slight exotherm was observed which increased to a maximum temperature of 56° C. and a pressure of 965 kPa over a 9 minute period. Following the exotherm the reactor was held at 42° C. for 6 hours while the mixture was agitated. The reactor was then vented of excess HFP (with the recovery of 0.7 g HFP) and the contents of the reactor were decanted to yield 103.8 grams (g) of a two phase reaction product. The upper layer (90.6 g) was separated from the lower layer, washed with concentrated sulfuric acid to remove residual $SO_3$ and then distilled to give 63.3 grams of HFP suitone (66% yield with respect to the consumed olefin) with boiling point (b.p.) 45°–50° C. NMR analysis of a higher boiling fraction (b.p. 50°–167° C., yield 25 g) revealed a mixture oftetrafluoropropionic acid derivatives and fluorosulfonic acid. A small portion of this fraction was refluxed in methanol for one hour to give tetrafluoropropionic acid methyl ester (yield 12% based on hexafluoropropene consumed). HFP sultone, after heating with concentrated sulfuric acid for 17 hours at 40° C., was recovered by distillation with 95% yield.

EXAMPLE 2

Preparation of HFP sultone from the reaction of excess hexafluoropropene with oleum at elevated pressure Using essentially the procedure of Example 1, the reactor was charged with 33.8 g of 67 wt. % oleum (0.28 mole $SO_3$) and 58.0 g hexafluoropropene. After the initial exotherm (max. pressure 896 kPa at 39° C.) the mixture was heated for 13 hours at 43° C. The reactor was vented of excess hexafluoropropene (16.0 g recovered including HFP collected during followed distillation). There was consumed 42.0 g (0.28 mole) HFP. The two phase reaction solution (70.1 g) was distilled using a concentric tube column to yield HFP sultone (39.8 g, 62% yield based on HFP consumed, b.p. 47° C.). The distillation residue was then distilled using a mini-lab apparatus to give 5.4 g of an intermediate fraction with a b.p. of 56°–155° C., 20 g of a fraction with a b.p. of 156°–167° C., and 1.3 g ofundistilled residue. The fraction with b.p. 156°–167° C. was analyzed by $^{19}F$ and $^{1}H$ NMR to reveal a complex mixture of primarily fluorosulfonic acid and several acid fluorides, sulfonyl fluorides, and at least three tetrafluoropropionic acid derivatives of the structure $CF_3CHFCOX$, where X=F, $OSO_2F$ and possibly OCOCH-$FCF_3$. The molar ratio of $HSO_3F$ to all CHF compounds was 88:35.

EXAMPLE 3

Preparation of HFP sultone from the reaction of excess hexafluoropropene at elevated pressure and in solvent.

Using essentially the procedure of Example 1, the reactor was charged with 44.7 g hexafluoropropene, 45.9 g of 67 wt. % oleum and 41.5 g Fluorinert FC-77™. The reaction mixture was heated at 50° C. for 6 hours. The reactor was vented of excess HFP and the sultone layer (95.0 g) was separated and distilled to provide the HFP sultone (45 g, b.p. 48°–52° C., purity 93% by gc). The yield was 65% based on consumed HFP.

EXAMPLE 4

Preparation of 1H-tetrafluoroethanesulfonyl fluoride from the reaction of hexafluoropropene with oleum at elevated pressure A 100 ml Parr reactor was charged with 62.4 g of 65 wt % oleum (0.51 mole $SO_3$) followed by 54.0 g (0.36 mole) hexafluoropropene, and reacted as described in Example 1. After the initial exotherm, the mixture was held at 47° C. for 3 hours. The reactor was vented and the two-phase reaction product (112.9 g) was separated. The sultone layer (86 g) was added drop-wise to 100 ml stirred, cold (0° C.) water in a 3-necked flask equipped with an agitator, an addition funnel and a dry-ice condenser. After complete addition of the suitone to water, the solution had separated into two layers. The lower layer was separated from the upper layer, washed with water, and dried to give 40.2 g (60% yield based on consumed olefin) of 1H-tetrafluoroethanesulfonyl fluoride of 99.4% purity as measured by gas chromatography.

EXAMPLE 5

Preparation of 1H-tetrafluoroethanesulfonyl fluoride from the reaction of hexafluoropropene with oleum, in the presence of a solvent, at elevated pressure Using essentially the procedure of Example 4, the reactor was charged with 54.4 g hexafluoropropene, 40.6 g of 67 wt. % oleum (0.34 mole $SO_3$) and 31.4 g Fluorinert FC-77™. The reaction mixture was heated at 50° C. for 4 hours, cooled, and the reactor vented of excess hexafluoropropene. There was consumed 52.0 g (0.35 mole) ItFP. The two phase contents of the reactor (117.2 g) was decanted, the upper suitone layer separated, the lower layer extracted with two equal volumes of FC-77™, and the extracts combined with the sultone layer. This layer was hydrolyzed by drop-wise addition into 25 ml of water at 0° C., washed, dried, and distilled using a concentric tube column to give 43.8 g 1H-tetrafluoroethanesulfonyl fluoride and FC-77™ (77:23 gc %) mixture with b.p. 63°–64° C. The yield of the sulfonyl fluoride was 51% based on the amount of consumed hexafluoropropene.

EXAMPLE 6

Preparation of 1H-tetrafluoroethanesulfonyl fluoride from the reaction of hexafluoropropene with oleum, in the presence of a solvent, and at atmospheric pressure Hexafluoropropene from a gas cylinder was bubbled through a mixture of 40 g of 67 wt. % oleum (0.33 mole $SO_3$) and 41.6 g 3M Fluorinert FC-77™ in a round bottom flask fitted with a 0° C. condenser and a –78° C. condenser in series. After ten hours, 27.2 g (0.18 mole) of hexafluoropropene was consumed. The product sultone was hydrolyzed and further purified as in Example 5 to give a 32.5 g mixture of 70.5 gc % of the tetrafluoroethanesulfonyl fluoride and 28.5% FC -77 with b.p. 63°–65° C. The yield of the sulfonyl fluoride was 63% based on the amount of consumed hexafluoropropene.

EXAMPLE 7

Preparation of 2H-pentafluoropropene (PFP) beta-sultone 2H-pentafluoropropylene (8.4 g) was evaporated from a cold (–78° C.) trap and bubbled through 7.1 g of 67 wt. % oleum (59.5 mmole $SO_3$), in a flask fitted with a magnetic stirrer and two condensers in series at –8.5° C. and –78° C., and capped with a cold-finger trap maintained at –78° C. A slight exotherm subsided after 2.5 hours and the unreacted 2H-pentafluoropropylene (0.73 g) was purged with nitrogen into the end trap. There was consumed 7.92 g (60.0 mmole) of the PFP. The reaction mixture was distilled to provide a first fraction (9.3 g, b.p. 88°–117° C.), and a second fraction (3.89 g) offluorosulfonic acid with a b.p. of 154°–165° C. NMR analysis of the first fraction revealed a complex mixture containing $CF_3CH_2COF$ (4.7% mole percent), 2H-pentafluoropropylene suitone (35.8%), the linear isomer of 2H-pentafluoropropene sultone (9%) and 2,2-dihydropentafluoropropyl-1-fluorosulfate (14.1%).

In another experiment using essentially the same procedure, 2H-pentafiuoropropene (22 g) was bubbled through 20.2 g of 67 wt. % oleum (0.17 mole $SO_3$). The 2H-pentafluoropropene that collected in the cold finger was returned to the reactor. After three passes over four hours the absorption of the propene ended and a total of 18.6 g (0.14 mole) had been consumed. The reaction mixture (39.8 g) was distilled to provide a first fraction containing the desired sultone (25.0 g, b.p. 38°–74° C. at 25 torr) and a second fraction offluorosulfonic acid (9.7 g, b.p. 165°–168° C.). Redistillation of the first fraction on a concentric tube column gave $CF_3CH_2COF$ (1.99 g, 11% yield, b.p. 49°–52° C.), PFP suitone, and the isomeric open chain version of the PFP suitone FC(O)CH(CF3)$SO_2$F (10.3 g, 34% yield, b.p. 85°–87° C.). Also isolated by distillation was $CF_3CH_2CF_2OSO_2F$ (3.94 g, 12% yield, b.p. 92°–108° C., purity 67%).

EXAMPLE 8

Preparation of 6H-undeca-1-hexene beta-sultone

6H-Undecafluoro-1-hexene (2.27 g, 8 mmole) and 1.57 g of 65% oleum (13 mmole $SO_3$) were heated in a sealed glass tube for 13 hours at 100° C. to produce a two-phase reaction product. The upper, sultone layer (2.69 g) was separated, washed with concentrated sulfuric acid, and distilled to yield 2.25 g of 2-hydroxy-1-(4H-perfluorobutyl)-1,2,2-trifluoroethanesulfonic acid sultone. Yield 77% based on 6H-undecafluoro-1-hexene, b.p. 40° C. at 13 torr. $^{19}$F NMR: –137.3 (d $CHF_2$, JHF 52.0 Hz), –129.24 m and –129.68 m ($CF_2$, ABq JFF 299 Hz), –121.15 m and –121.65 m ($CF_2$, ABq, JFF 306 Hz), –116.78 m and –118.07 m ($CF_2$, ABq, JFF 313 Hz), –151.5 m (CF), –82.56 m and –85.88 m ($OCF_2$, ABq, JFF 108 Hz). Anal. Calc. for $C_6HF_{11}O_3S$: C 19.9; S 8.8. Found: C 19.6; S 8.7.

EXAMPLE 9

Into an electrochemical fluorination cell of the type described in U.S. Pat. No. 2,713,593 containing anhydrous hydrogen fluoride, was fed: 1H-tetrafluoroethane sulfonyl fluoride (7607 g, prepared essentially as described in Example 4); and perfluoro ethyltetrahydrofuran (approx. 7000 g) in a continuous manner over a period of 243 hours. At the same time, the resultant hydrogen fluoride solution was electrolyzed at an average voltage of 7.0 volts, and an average current density of 270 amps/$m^2$, and at 55° C. and 45 psig (0.31 MPa). The gaseous products were passed through a –40° C. condenser whereby the liquefied hydrogen fluoride was returned to the cell and most of the desired product was collected (perfluoroethanesulfonyl fluoride, 6300 g, 76% of theoretical yield) along with the inert diluent. Uncondensed gaseous products were then passed to a dry ice trap where additional product was collected (10% reported).

What is claimed is:

1. A process for preparing a fluorinated beta-sultone, the process comprising the step of reacting a fluorinated olefin hav. ing at least three carbon atoms with oleum.

2. The process of claim 1, wherein the fluorinated olefin is a 1,1-difluoro terminal olefin.

3. The process of claim 1, wherein the fluorinated olefin is a 1,1-difluoro terminal olefin having the general formula:

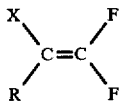

wherein X is F or H, and R is a straight or branched haloalkyl or perhaloalkyl group.

4. The process of claim 3, wherein R is a haloalkyl or perhaloalkyl group having from about 1 to 10 carbon atoms.

5. The process of claim 3, wherein R is a haloalkyl or perhaloalkyl group having from about 1 to 6 carbon atoms.

6. The process of claim 3, wherein the 1,1-difluoro terminal olefin is chosen from the group consisting of hexafluoropropene, 6H-perfluoro-1-hexene, and 2H-pentafluoropropene.

7. The process of claim 1, wherein the oleum comprises less than about 75 parts by weight $SO_3$ per 25 parts by weight $H_2SO_4$.

8. The process of claim 1, wherein the oleum comprises from about 50 to 70 parts by weight $SO_3$ per 50 to 30 parts by weight $H_2SO_4$, respectively.

9. The process of claim 1, wherein the oleum comprises from about 60 to 70 parts by weight $SO_3$ per 40 to 30 parts by weight $H_2SO_4$, respectively.

10. The process of claim 1, wherein the oleum and the fluorinated olefin are combined to provide a reaction solution having a molar ratio of sulfur trioxide versus fluorinated olefin in the range from about 1:2 to 2:1.

11. The process of claim 1, wherein the oleum and the fluorinated olefin are combined to provide a reaction solution having a molar ratio of sulfur trioxide versus fluorinated olefin in the range from about 9:10 to 10:9.

12. The process of claim 1, wherein the reaction is performed in a pressurized reaction vessel, beginning at temperature of about 35° C. and a pressure of about 760 torr.

13. The process of claim 1, wherein the fluorinated beta-sultone has the general formula:

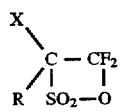

wherein X and R are defined as in claim 3.

14. The process of claim 13, wherein the fluorinated beta-sultone is chosen from the group consisting of hexafluoropropene beta-sultone, 6H-undecafluoro-1-hexene beta-sultone, and 2H-pentafluoropropene beta-sultone.

15. The process of claim 1, further comprising the step of hydrolyzing the fluorinated beta-sultone to produce a fluoroalkanesulfonyl fluoride.

16. The process of claim 15, wherein the fluoroalkanesulfonyl fluoride is chosen from the group consisting of 1H-tetrafluoroethanesulfonyl fluoride, 2,2,2-trifluoroethanesulfonyl fluoride, and 1,5-dihydrononafluoropentane sulfonyl fluoride.

17. The process of claim 1, comprising the step offluorinating the fluorinated beta-sultone to produce a perfluoroalkanesulfonyl fluoride.

18. A process for preparing a fluoroalkanesulfonyl fluoride comprising the steps of:

reacting a fluorinated olefin having at least three carbon atoms with oleum to produce a fluorinated beta-sultone, and hydrolyzing the fluorinated beta-sultone to produce a fluoroalkanesulfonyl fluoride.

19. A process for preparing a fluoroalkyl sulfonyl acid salt comprising the steps of:

reacting a fluorinated olefin having at least three carbon atoms with oleum to produce a fluorinated beta-sultone, and hydrolyzing the fhorinated beta-sultone to produce a fiuoroalkyl sulfonyl acid salt.

* * * * *